(12) United States Patent
Rose

(10) Patent No.: US 7,157,055 B2
(45) Date of Patent: Jan. 2, 2007

(54) APPARATUS FOR SAMPLE HANDLING FOR AN INJECTION SYSTEM OF A CHROMATOGRAPH

(75) Inventor: Bernhard Rose, Düsseldorf (DE)

(73) Assignee: Gerstel Systemtechnik GmbH & Co., Mulheim (DE)

( * ) Notice: Subject to any disclaimer, the term of this patent is extended or adjusted under 35 U.S.C. 154(b) by 323 days.

(21) Appl. No.: 10/372,038

(22) Filed: Feb. 21, 2003

(65) Prior Publication Data

US 2003/0180185 A1    Sep. 25, 2003

(30) Foreign Application Priority Data

Mar. 7, 2002   (DE) .................................. 102 10 048

(51) Int. Cl.
*G01N 30/04*    (2006.01)
(52) U.S. Cl. .................... 422/89; 422/63; 422/99; 422/100; 422/104; 73/23.41; 95/89; 96/105
(58) Field of Classification Search ............... 73/23.41, 73/863, 863.11, 863.91, 864.31, 864.83, 864.84; 95/82, 87, 89; 96/101, 105; 422/63, 99, 422/100, 104, 89
See application file for complete search history.

(56) References Cited

U.S. PATENT DOCUMENTS 3,067,016 A * 12/1962  Rozycki ..................... 422/104
4,715,413 A * 12/1987  Backlund et al. ............. 141/94
5,429,010 A *  7/1995  Lohndorf et al. .......... 73/866.5
5,588,988 A    12/1996  Gerstel et al.

FOREIGN PATENT DOCUMENTS

DE        44 19 596 C1    6/1995

* cited by examiner

*Primary Examiner*—Jan M. Ludlow
(74) *Attorney, Agent, or Firm*—Patterson, Thuente, Skaar & Christensen, P.A.

(57) ABSTRACT

The invention relates to an apparatus for sample preparation and/or sample delivery for an injection system of a chromatograph, having a magazine (1), which can be moved in steps, for juxtaposed sample tubes (2), and having a lifting device (6) which can be moved between two end positions perpendicular to the transport direction of the magazine (1) via a motor (11) and bears a gripper (7) for a sample tube (2), as well as having a transfer device for a sample tube (2), the lifting device comprising at least one telescopic threaded cylinder (8) which bears the gripper (7) and has a plurality of nested threaded cylinders with an inner threaded cylinder (8*a*) and an outer threaded cylinder (8*d*) of which one is arranged non-rotatably relative to the magazine (1), while the other can be rotated by the motor (11).

15 Claims, 8 Drawing Sheets

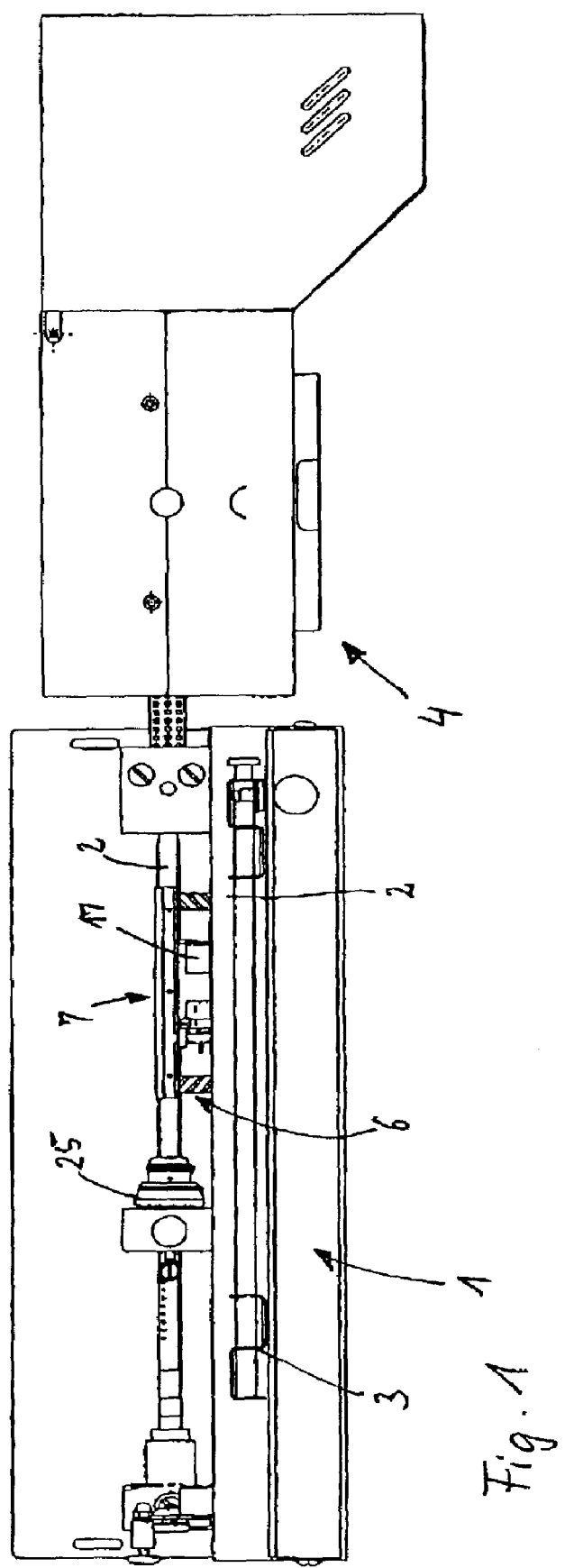

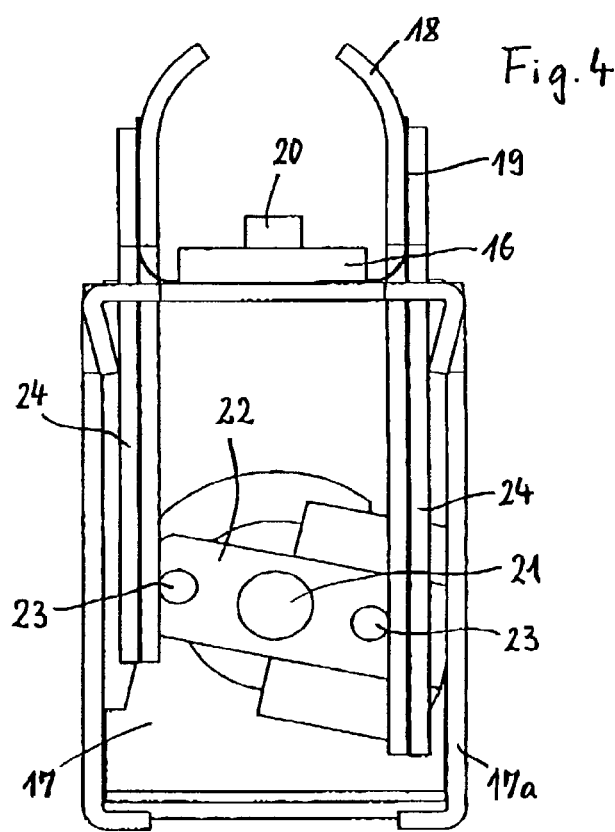
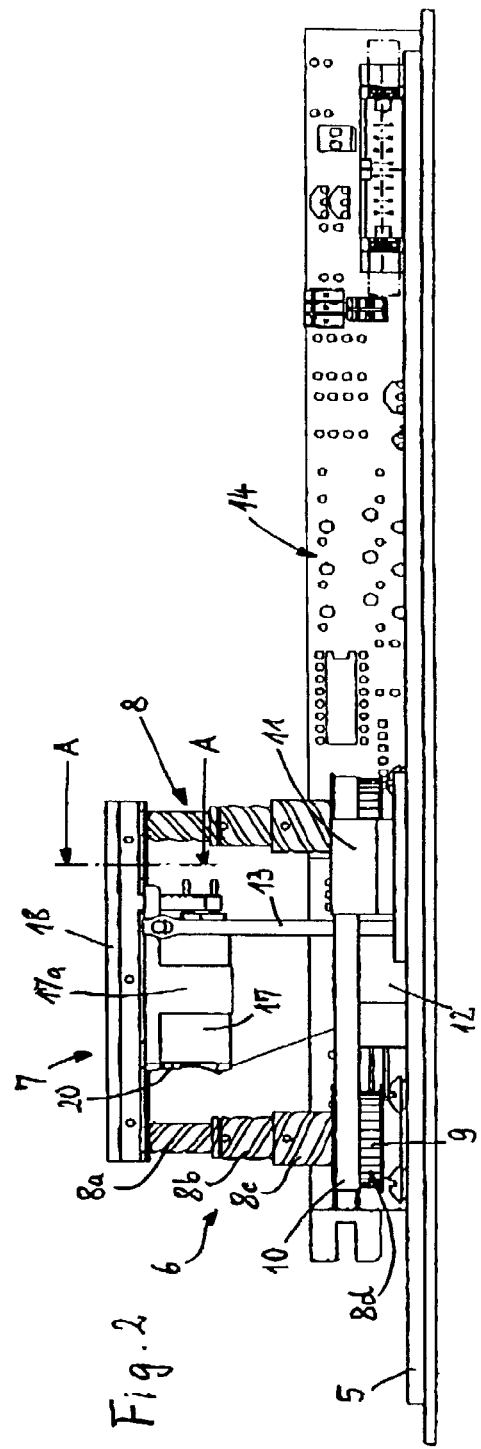

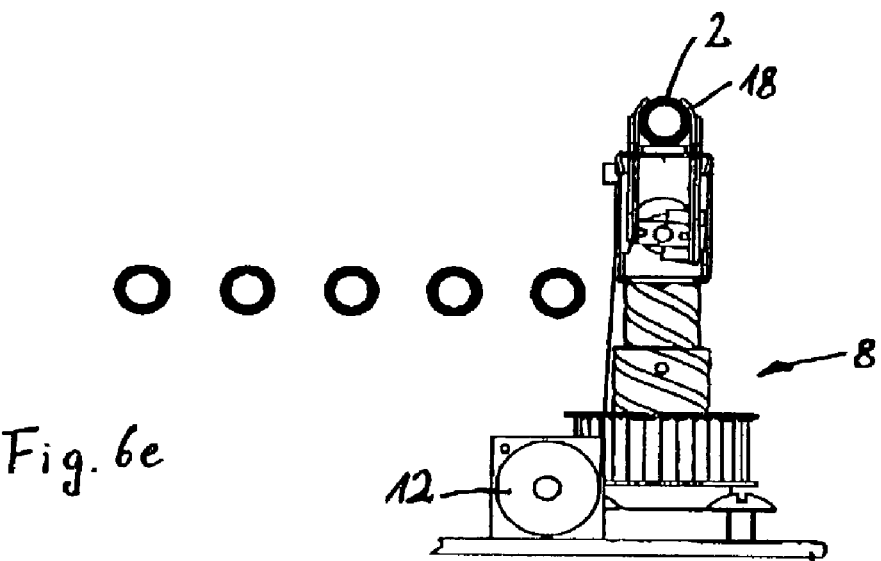
Fig. 6e
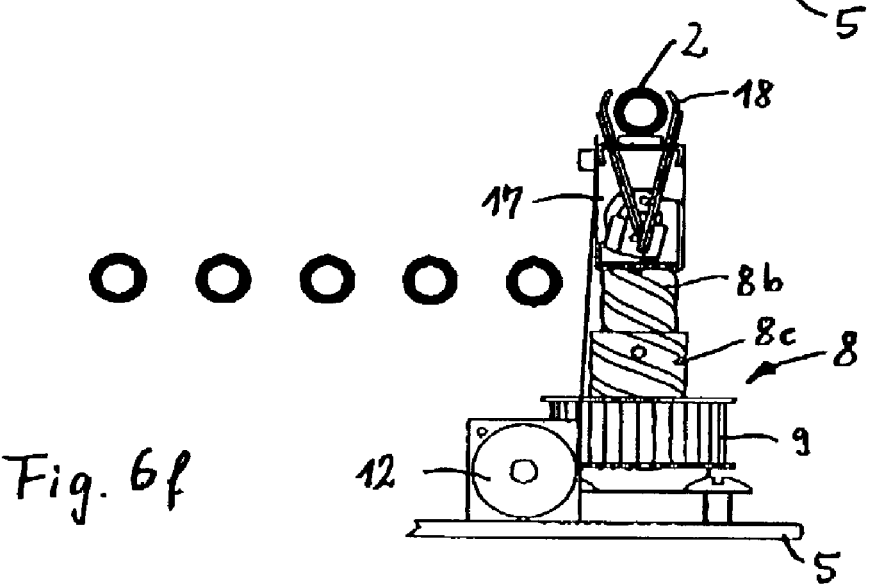
Fig. 6f
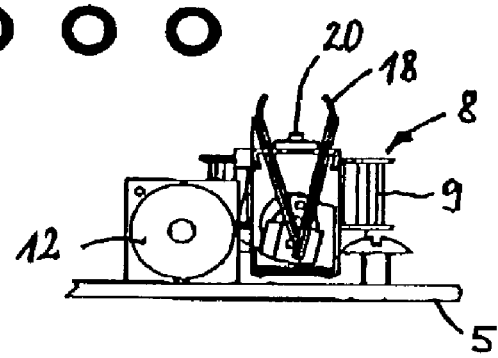
Fig. 6g

APPARATUS FOR SAMPLE HANDLING FOR AN INJECTION SYSTEM OF A CHROMATOGRAPH

FIELD OF THE INVENTION

The invention relates to an apparatus for handling samples for an injection system of a chromatograph for at least one of handling action of the group of sample preparation and sample delivery. Such a sample delivery apparatus serves the purpose of extracting sample tubes from a magazine and transferring them into an injection system of a chromatograph, for example a liquid or gas chromatograph.

BACKGROUND OF THE INVENTION

It is known that samples contained in the sample tubes can, for example, be subjected there to thermodesorption as described, for example, in German Patent DE 44 19 596 C1. After the extraction of the sample tubes from the magazine, the former have to be lifted out of the plane of the magazine. It is known for this purpose to provide a lifting device which can be adjusted between two end positions and has a holding device for a sample tube. The lifting device is formed in this case by a motor-operated shearing mechanism. However, the latter is sensitive and not very stable and therefore liable to failure.

SUMMARY OF THE INVENTION

It is therefore an object of the invention to provide a robust and strong apparatus for handling samples for an injection system of a chromatograph.

Thus, the invention concerns an apparatus for handling samples for an injection system of a chromatograph in the form of sample preparation and/or sample delivery, said apparatus having a magazine, which is moveable in steps, for juxtaposed sample tubes, and having a lifting device which is moveable between two end positions perpendicular to the transport direction of the magazine via a motor and bears a gripper for a sample tube, as well as having a transfer device for a sample tube, wherein the lifting device comprises at least one telescopic threaded cylinder which bears the gripper and has a plurality of nested threaded cylinders with an inner threaded cylinder and an outer threaded cylinder of which one is arranged non-rotatably relative to the magazine, while the other is rotateable by the motor.

The fact that use is made of a lifting device which comprises at least one telescopic threaded cylinder which has in each case a plurality of nested threaded cylinders, of which the inner threaded cylinder is arranged non-rotatably, while the outer threaded cylinder can be rotated by motor, results in a stable and robust design which is correspondingly not very liable to failure.

When two mutually spaced telescopic threaded cylinders are used, their outer threaded cylinders can be driven synchronously for a parallel movement, or asynchronously for an angularly displaced movement.

Further embodiments, objects and advantages of the invention are to be gathered from the following description and the claims.

BRIEF DESCRIPTION OF THE DRAWINGS

The invention is explained in more detail below with the aid of exemplary embodiments represented in the attached illustrations.

FIG. 1 shows in a schematic front view an apparatus for sample preparation and/or sample delivery for an injection system of a gas chromatograph.

FIG. 2 shows a side view of a lifting device in an extended position for an apparatus for sample preparation and/or sample delivery for an injection system of a gas chromatograph.

FIG. 4 shows an enlarged section along the line A—A of FIG. 2.

FIGS. 6a to 6g show an operating cycle of a gripper of the lifting device in schematic form.

DETAILED DESCRIPTION OF PREFERRED EMBODIMENTS

Figure 3:
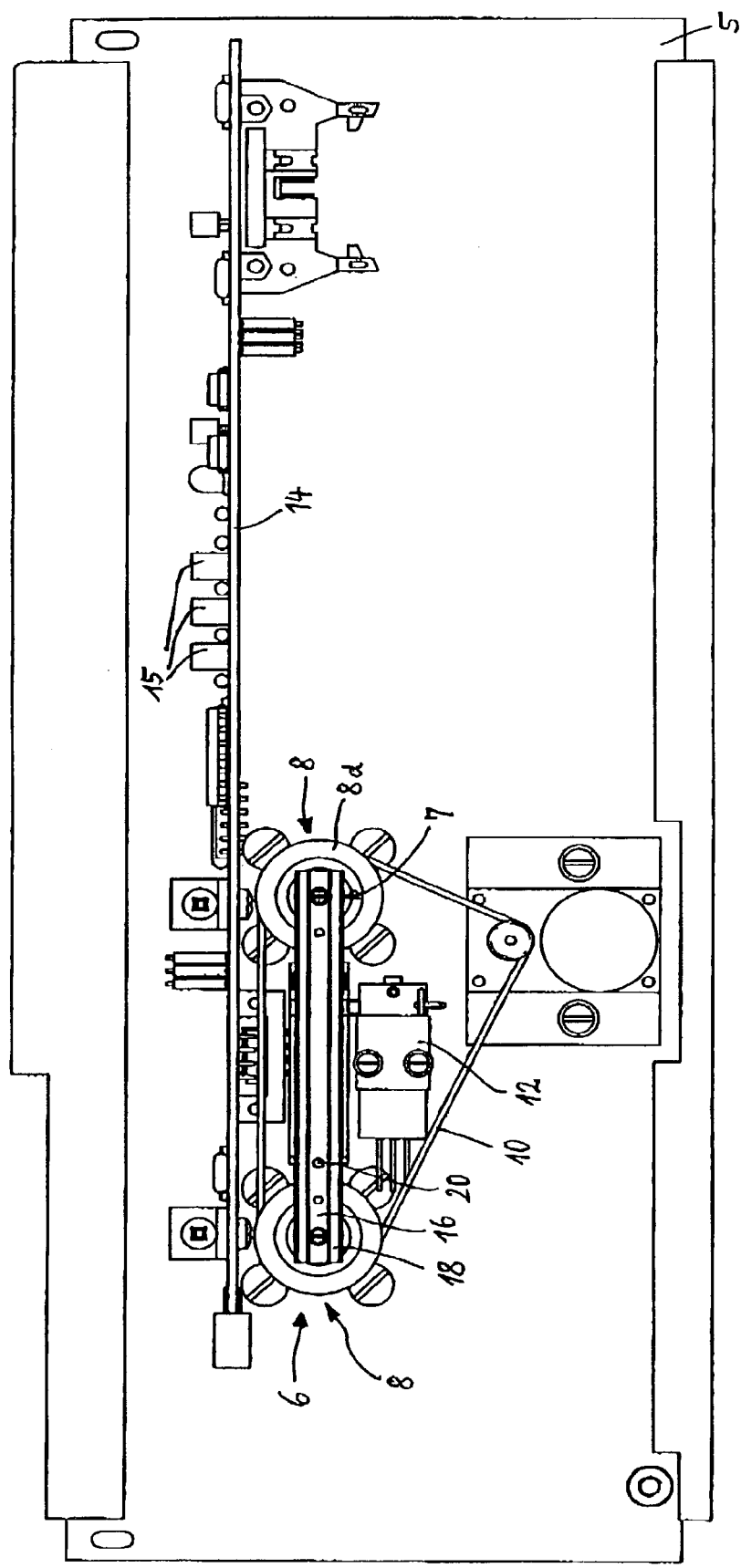
FIG. 3 shows a top view of the lifting device of FIG. 2.

The apparatus illustrated in FIG. 1 comprises a magazine 1 which can be moved horizontally (perpendicular to the plane of the paper in FIG. 1) and in steps, and which accepts sample tubes 2 by means of clamps 3 parallel to one another traverse to the direction in which the magazine 1 can be moved and in a horizontally arranged fashion. Arranged next to the apparatus is a thermodesorption device 4 of a gas chromatograph into which sample tubes 2 are inserted successively from the magazine 1, and whose samples are subjected to a thermodesorption, after which the sample tubes 2 are subsequently transported back into the magazine 1.

The apparatus comprises a lifting device 6, arranged on a plate 5, with a gripper 7 for a sample tube 2.

In the exemplary embodiment illustrated, the lifting device 6 comprises two telescopic threaded cylinders 8 which are arranged at a spacing from one another and in each case have a plurality of, four in the case illustrated, nested threaded cylinders 8a, 8b, 8c, 8d which engage with one another via balls in order to be as easy to move as possible. Because the gripper 7 is fastened on the respectively inner threaded cylinders 8a, they are arranged non-rotatably relative to the plate 5. The respectively outer threaded cylinders 8d are provided on their outer circumference with a toothed rim 9 such that they can be driven jointly and therefore synchronously via a toothed belt 10 by an electric motor 11 with the aid of a downstream transmission.

Instead of the outer threaded cylinder 8d, it is also possible for the inner threaded cylinder 8a to be driven while the outer threaded cylinder 8d is stationary.

If only one telescopic threaded cylinder 8 is used, the inner threaded cylinder 8a is to be held non-rotatably relative to the plate 5 via, for example, a guide rod guided non-rotatably in the plate.

It is, furthermore, expedient, particularly in the case where not only the two end positions of the gripper 7, but also at least one position lying therebetween are to be capable of being driven, to provide on the plate 5 a rotation angle sensor 12 for monitoring the extension of the telescopic threaded cylinders 8. Fastened by suspension on the gripper 7 is an extractable transmission belt 13 of the rotation angle sensor 12, whose extracted length constitutes a measure of the extension of the telescopic threaded cylinders 8.

Located on the plate 5 is a printed circuit board 14 with electric components for controlling the movement of the lifting device 6 and of the gripper 7. This also includes trimmers 15 corresponding in number to the number of the positions which the lifting device 6 is to approach and which can be set via the trimmers 15.

Figure 6A:
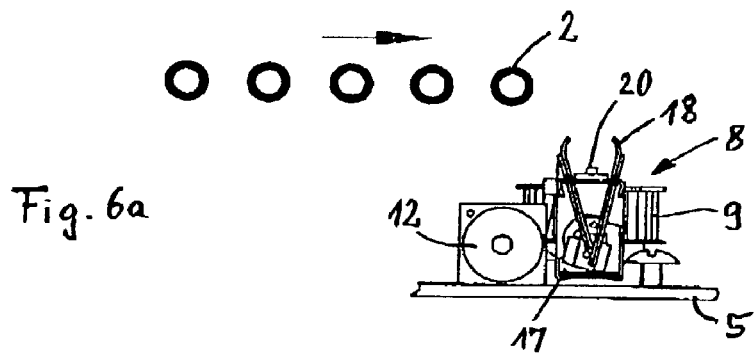
Figure 6B:
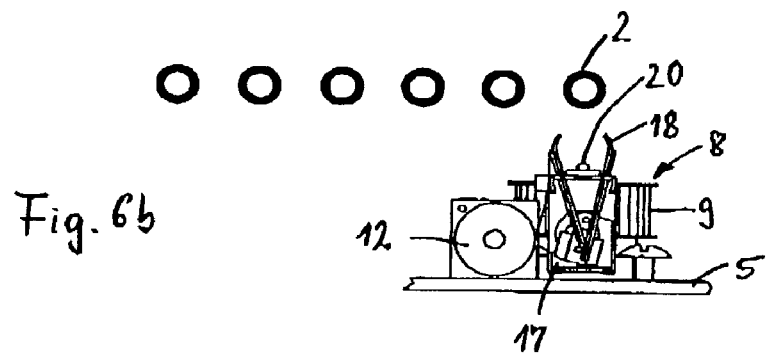
Figure 6C:
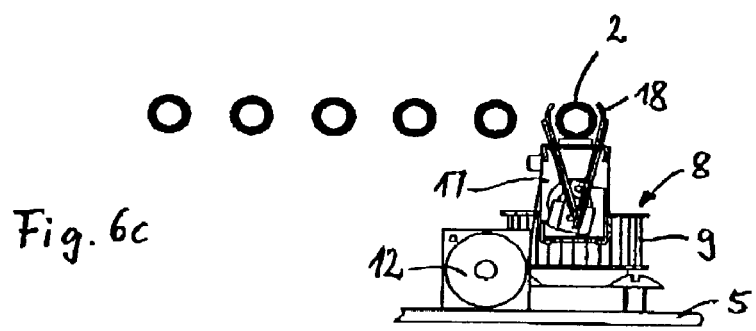
Figure 6D:
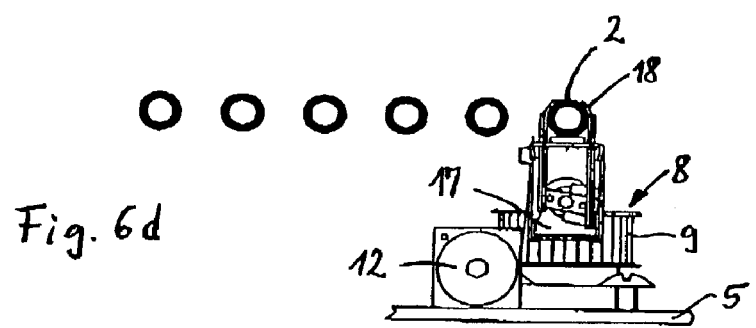

The gripper 7 comprises an elongated rail 16 which is fastened on the inner threaded cylinders 8a and bears on the underside an electric motor 17 via a holder 17a. Two gripper clamps 18 projecting over the rail 16 are suspended opposite to one another on the rail 16 and are biased in the opening direction via a plurality of U-shaped spring sheets 19, that is to say the spring action of the limbs of the spring sheets 19 is directed outwards. Arranged on the rail 16 is a microswitch 20 which is actuated by a sample tube 2 picked up by the gripper 7. In such a case, the microswitch 20 triggers the electric motor 17, whose shaft 21 bears a locking device in the form of a plate 22 with pins 23. The pins 23 engage with limbs 24 which are connected to the gripper clamps 18 and project into the region of the pins 23, one limb 24 being shorter than the other such that in the open position of the gripper clamps 18 the limbs abut one another, whereas the pins 23 can engage separately with the two limbs 24, compare, for example, FIG. 6a. The gripper clamps 18 are brought into engagement with a sample tube 2 located therein by rotation by 90°, and held, compare, for example, FIG. 4 or 6d.

The spreading device can also comprise a cam disc.

Figure 5A:
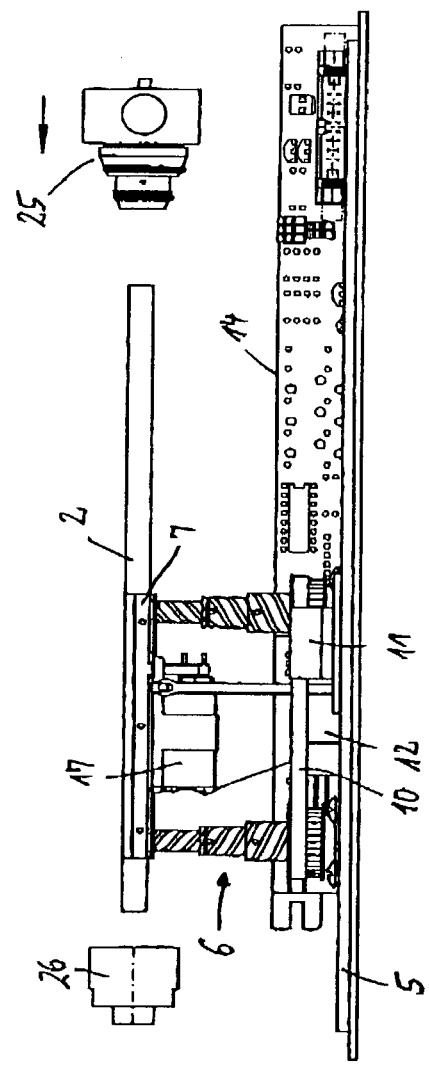
FIGS. 5a and 5b show a transfer of a sample tube in schematic form.
Figure 5B:
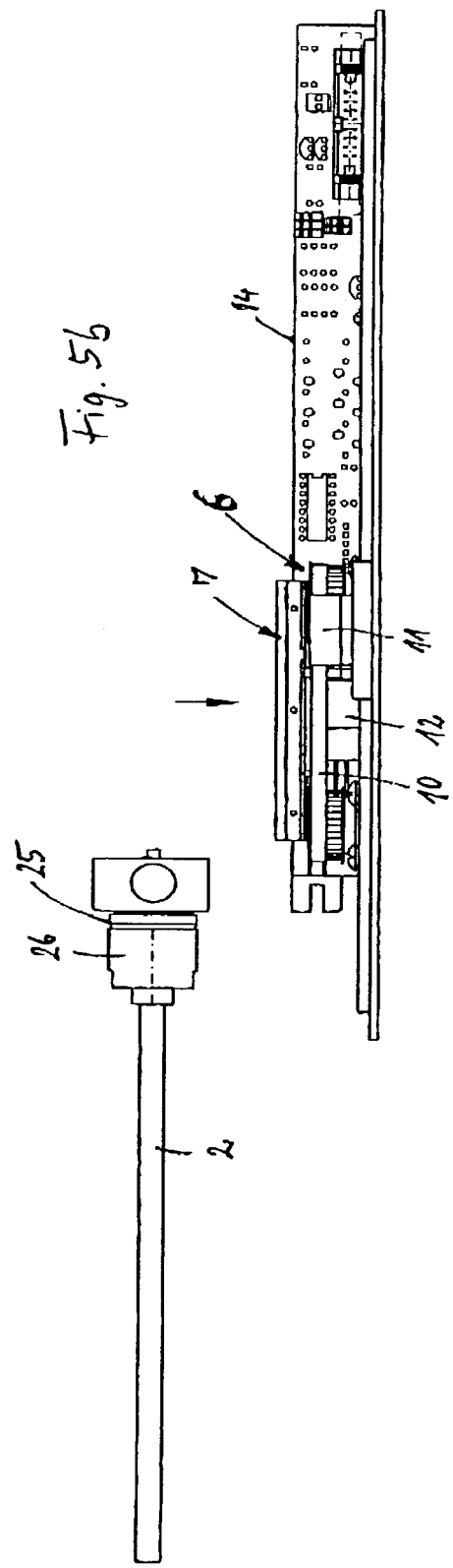

A transfer device for transferring a sample tube 2 gripped by the gripper 7 comprises a locking cone 25 which can be moved in stages in the longitudinal direction, for example by means of a guided carriage, a spindle or the like, and has seals, compare FIGS. 5a, 5b. The locking cone 25 accepts an end of the sample tube 2 held by the gripper 7, whereupon the gripper 7 opens and releases the sample tube 2 for further transport into the thermodesorption device 4, whose valve head receptacle 26 is shown in FIGS. 5a, 5b. In this case, the lifting device 6 moves back into the initial position so that the locking cone 25 can pass.

The cycle of motion of the lifting device 6 and of the gripper 7 is illustrated in steps in FIGS. 6a to 6g. In accordance with FIG. 6a, the lifting device 5 is in its lower retracted position. The gripper 7 is open. The magazine 1 is moved one step further and thus over the gripper 7 such that a sample tube 2 is located above the latter, FIG. 6b. The lifting device 6 is raised into an intermediate position in which the sample tube 2 is picked up by the gripper 7 and actuates the microswitch 20, FIG. 6c. The latter initiates a 90° rotation of the electric motor 17 and thus a closure of the gripper 7, which is held in this position, FIG. 6d. Thereafter, the lifting device 6 is raised into its upper end position, FIG. 6e. The sample tube 2 is gripped by the locking cone 25 at one end and the gripper 7 is opened by the electric motor 17, FIG. 6f. The lifting device 6 moves into its lower end position, so that the locking cone 25 can pass.

After the thermodesorption has been undertaken, the sample tube 2 is recovered in the opposite direction and deposited in the magazine 1, after which the entire operation is repeated.

Instead of a thermodesorption device 4, it is also possible to use any other desired injection device for a chromatograph or a sample preparation apparatus into which and from which sample tubes 2 can be introduced and removed.

Figures 7, 8, 9, 10:
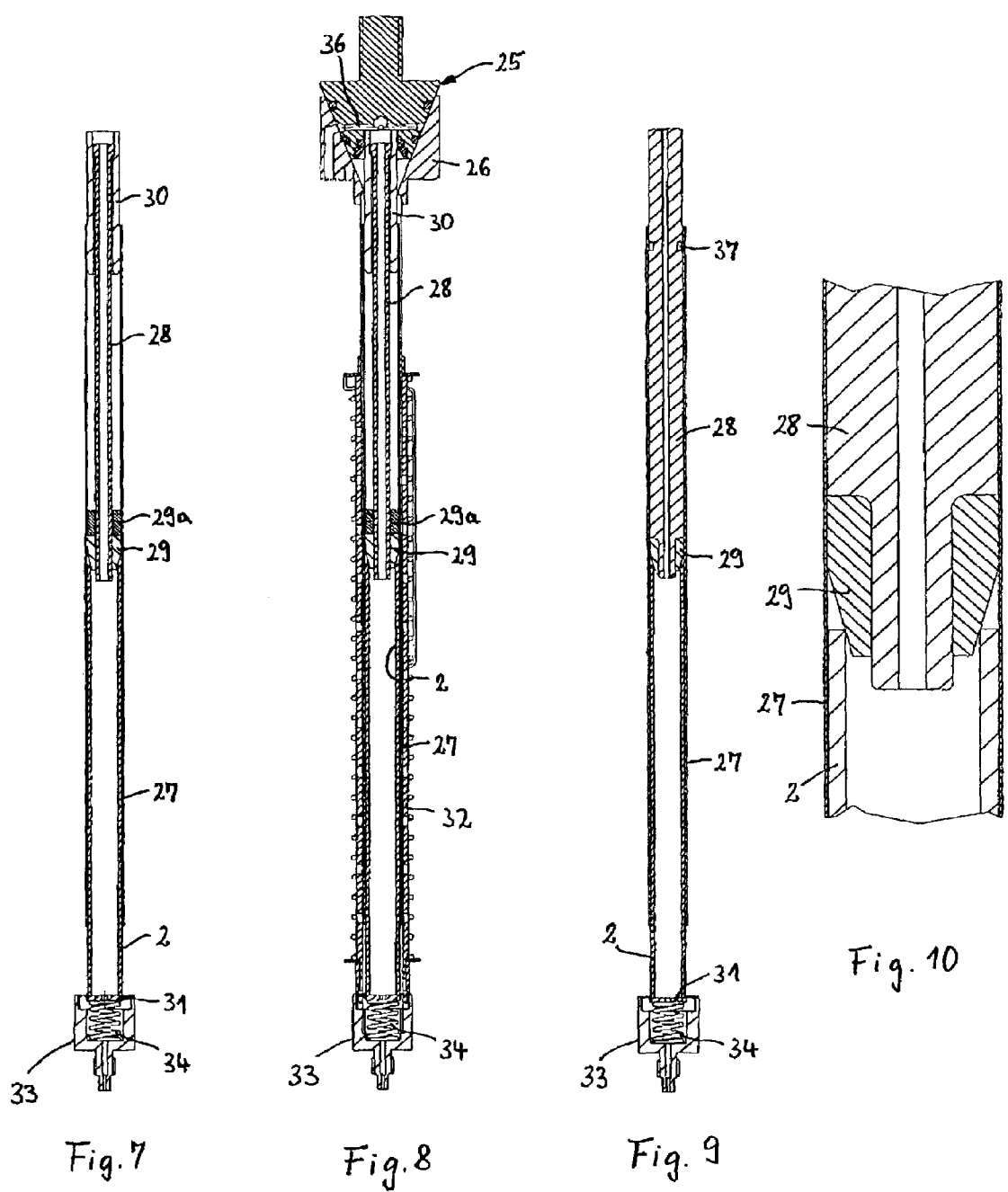
FIG. 7 shows a section of a sample tube with adapter.
FIG. 8 shows the sample tube with adapter of FIG. 7 inserted into a thermodesorption device (of which only a detail is shown).
FIG. 9 shows a section of a further embodiment of a sample tube with adapter.
FIG. 10 shows an enlarged detail from FIG. 9.

In accordance with FIGS. 7, 8, the sample tube 2 is bonded in a metal positioning tube 27 which simultaneously accepts a carrier gas tube 28, coaxial therewith, via a sealing cone 29 and a spacing sleeve 29a at one end, and a receptacle 30, connected to the carrier gas tube 28 by bonding, for example, for the locking cone 25 at the other end. The receptacle 30 projects from the positioning tube 27 in order to be able to be brought into engagement with the locking cone 25 in a sealed fashion. The sealing cone 29 is seated in the sample tube 2. Moreover, the sample tube 2 has a pressure plate 31, provided with a small through-opening, on its side averted from the locking cone 25. Upon being inserted, for example into a heatable tube 32 of the thermodesorption device 4, the said pressure plate presses against a spring 34 held by a connecting piece 33, as a result of which the seal between the sample tube 2 and carrier gas tube 28 is ensured during the thermodesorption. A receptacle 26 of the thermodesorption device 4 is provided with a bore 35 for supplying the carrier gas which communicates with a bore 36 in the locking cone 25 from which supplied carrier gas passes into the carrier gas tube 28 in order to lead off desorbed substances through the connecting piece 33.

In accordance with FIGS. 9, 10, the carrier gas tube 28 fills up the positioning tube 27 and is provided with a circumferential groove 37 where the positioning tube 27 is flanged in. The locking cone 25 thereby directly holds the carrier gas tube 28.

Figure 11:
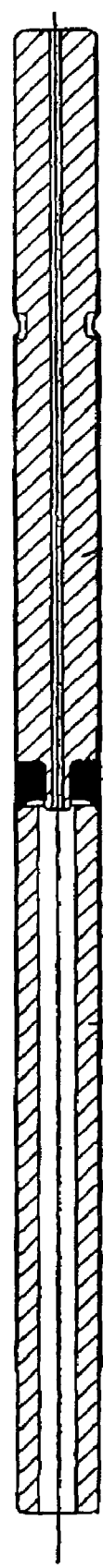
FIG. 11 shows an additional embodiment of a sample tube with adapter.
Figure 12:
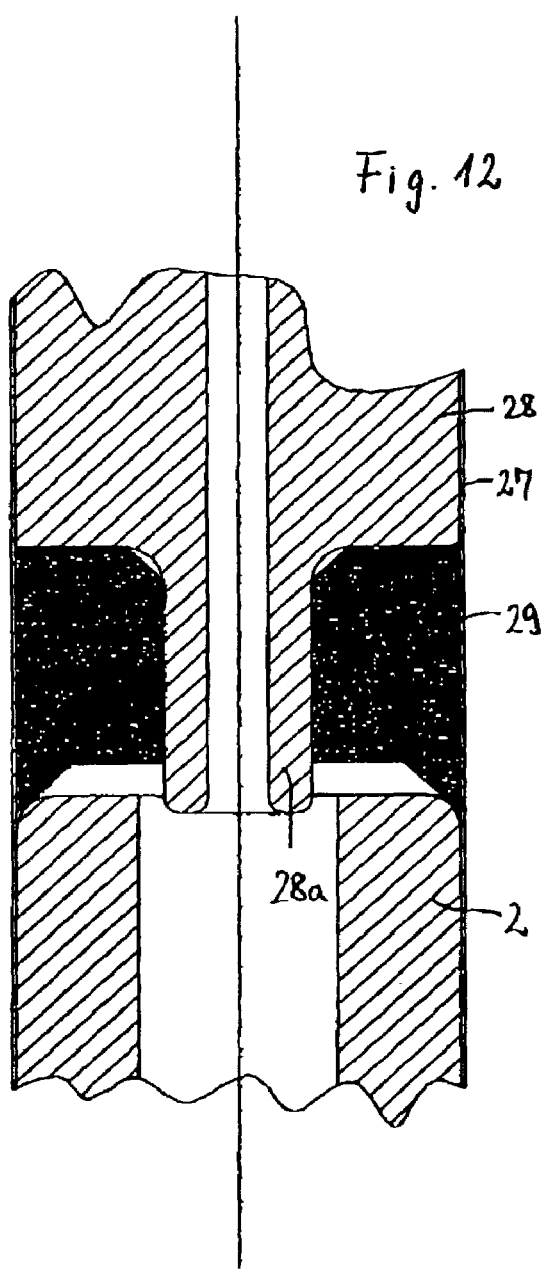
FIG. 12 shows an enlarged detail from FIG. 11.

In the embodiment illustrated in FIGS. 11, 12, the seal 29 embraces the sample tube 2 conically, on the outside. For this purpose, the carrier gas tube 28 has a projection 28a onto which is pushed the seal 29, which embraces the end of the sample tube 2 with its sealing cone.

The seal 29 effects a gas-tight connection between the sample tube 2 and carrier gas tube 28 such that no ambient flow takes place on the outer circumference, as a result of which contaminants, such as fingerprints, located on the outer surface cannot impair the sample analysis.

Consequently, it is possible for different sample tubes 2 to be handled with the aid of the same apparatus by using a positioning tube 27.

What is claimed is:

1. An apparatus for handling samples for an injection system of a chromatograph, said samples being provided in sample tubes, comprising:

a magazine containing a plurality of the sample tubes in a juxtaposed manner, the magazine being moveable in steps in a transporting direction; a lifting device having two end positions and movable therebetween in a direction perpendicular to the transporting direction of the magazine, the lifting device being movable via a motor and bearing a gripper for one of the plurality of sample tubes; a transfer device, proximate the lifting device, for transferring one of the plurality of sample tubes from the gripper to the injection system in the transporting direction; wherein the lifting device comprises at least one telescopic threaded cylinder supporting the gripper, the at least one telescopic threaded cylinder comprising a plurality of nested threaded cylinders, the nested threaded cylinders comprising at least an outer and an inner threaded cylinder, one of the outer and inner threaded cylinders is arranged non-rotatably relative to the magazine, while the other of the outer and inner threaded cylinders is rotatable by the motor.

2. The apparatus according to claim 1, wherein two telescopic threaded cylinders support the gripper.

3. The apparatus according to claim 2, wherein the two telescopic threaded cylinders are driveable synchronously by the motor.

4. The apparatus according to claim 3, wherein the outer threaded cylinders are driveable jointly via a toothed belt.

5. The apparatus according claim 1, wherein the threaded cylinders interengage via balls.

6. The apparatus according to claim 1, wherein a rotation angle sensor is provided for monitoring the extension of the at least one telescopic threaded cylinder.

7. The apparatus according to claim 6, wherein an extractable transmission belt of the rotation angle sensor arranged on the magazine is fastened on the gripper.

8. The apparatus according to claim 1, wherein the gripper has two spring-biased gripper clamps and an electric motor engaging with the gripper clamps against the spring bias.

9. The apparatus according to claim 8, wherein the electric motor engages with limbs of the gripper clamps via a locking device.

10. The apparatus according to claim 8, wherein the gripper has a microswitch by means of which the electric motor can be started up upon acceptance of a sample tube.

11. The apparatus according to claim 8, wherein the gripper clamps are suspended with the aid of gripper clamp limbs on a rail and at least one substantially U-shaped leaf spring, the U-shaped leaf spring having a curved part adjoining two limbs, one on each of two sides of the curved part, the U-shaped leaf spring, being arranged transverse to the longitudinal direction of the gripper clamps and engaging with the gripper clamp limbs with the aid of said U-shaped leaf spring's limbs.

12. The apparatus according to claim 1, wherein the sample tube is provided with an adapter in the form of a positioning tube with a carrier gas tube inserted in a sealed fashion therein, the carrier gas tube further comprising a receptacle wherein the receptacle is adapted to receive the transfer device.

13. The apparatus according to claim 12, wherein the sample tube is bonded into the positioning tube.

14. The apparatus according to claim 12, wherein the carrier gas tube is flanged in the positioning tube.

15. The apparatus according to claim 12, wherein the sample tube is connected in a gas-tight fashion to the carrier gas tube via a seal with an inner or outer cone.

* * * * *